(12) United States Patent (10) Patent No.: US 8,569,513 B2
Tanaka et al. (45) Date of Patent: Oct. 29, 2013

(54) COMPOUND HAVING A TRIPTYCENE MOIETY

(75) Inventors: Satoshi Tanaka, Ashigarakami-gun (JP); Masaki Okazaki, Ashigarakami-gun (JP); Naoyuki Nishikawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 219 days.

(21) Appl. No.: 13/073,598

(22) Filed: Mar. 28, 2011

(65) Prior Publication Data

US 2011/0237804 A1 Sep. 29, 2011

(30) Foreign Application Priority Data

Mar. 29, 2010 (JP) ................................. 2010-075571

(51) Int. Cl.
*C07D 327/04* (2006.01)
(52) U.S. Cl.
USPC .......................................................... 549/31
(58) Field of Classification Search
USPC .......................................................... 549/31
See application file for complete search history.

(56) References Cited

U.S. PATENT DOCUMENTS 6,605,693 B1 8/2003 Becker et al.

FOREIGN PATENT DOCUMENTS

| JP | 2002-015871 A | 1/2002 |
|---|---|---|
| JP | 2002-532846 A | 10/2002 |
| JP | 2002-539286 A | 11/2002 |
| JP | 2004-182962 A | 7/2004 |
| JP | 2004-359599 A | 12/2004 |
| JP | 2008-308433 A | 12/2008 |
| WO | 00/36660 A1 | 6/2000 |

*Primary Examiner* — Taofiq A Solola
(74) *Attorney, Agent, or Firm* — Sughrue Mion, PLLC

(57) ABSTRACT

A compound having a triptycene moiety represented by formula (1) is disclosed. In the formula, $A^1$ and $A^2$ represent —S—, —O—, —CO—, or —NR—; $R^1$ and $R^3$ represent a substituent; n is an integer from 0 to 2; $R^4$ and $R^5$ an electron-withdrawing group having a Hammett's substituent constant $\sigma_p$ of equal to or more than 0; $L^{11}$, $L^{12}$, $L^{21}$ and $L^{22}$ represent a single bond or a divalent group selected from the group consisting of —O—, —S—, —S(=O)$_2$—, —CO—, —OCO—, —COO—, —OCOO— and —NR$^4$— where $R^4$ represents a $C_{1-7}$ alkyl group or hydrogen atom, —CH$_2$— and any combinations thereof; $Z^1$ and $Z^2$ represent a divalent 5- or 6-membered cyclic linking group; $R^{21}$ and $R^{22}$ represent a hydrogen atom or substituted or non-substituted alkyl group; and m1 and m2 each respectively represent an integer of from 0 to 2.

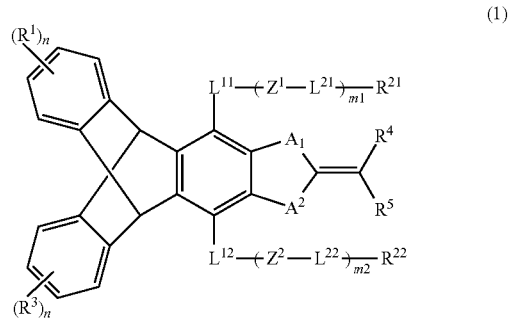

(1)

7 Claims, No Drawings

COMPOUND HAVING A TRIPTYCENE MOIETY

CROSS-REFERENCE TO RELATED APPLICATIONS

The present application claims the benefit of priority from Japanese Patent Application No. 2010-075571, filed on Mar. 29, 2010, the contents of which are herein incorporated by reference in their entirety.

BACKGROUND OF THE INVENTION

1. Field of the Invention

The present invention relates to a novel compound having a triptycene moiety.

2. Background Art

Triptycene derivatives are useful as functional materials. The applications of triptycene polymers to electroluminescence materials of illuminations or display devices have been studied (JP-T-2002-532846 and JP-T-2002-539286). It has been reported that such triptycene derivatives exhibit not only heat-resistant, transparent and low-refractive-index characteristics but also low-birefringent characteristics; and the applications of them to optical parts such as light waveguides, optical filters and lenses have been also studied (JP-A-2004-182962 and JP-A-2004-359599). Furthermore, the applications of triptycene derivatives to light-emitting devices (JP-A-2002-15871) or photoresist materials in the electricity and electron fields such as semiconductors and the optical fields (JP-A-2008-308433) have been also studied.

SUMMARY OF THE INVENTION

Many of the triptycene compounds, which have been proposed previously, are the compounds modified by introducing the substituent(s) on the benzene ring constituting the triptycene skeleton. Few triptycene derivatives, having the condensed triptycene skeleton with another ring, have been proposed. It has been unknown whether any unknown characteristics or improvement of the known characteristics can be achieved or not by fusing the triptycene skeleton to another ring.

One object of the present invention is to provide a novel compound having a triptycene moiety.

The means for achieving the object are as follows.

[1] A compound having a triptycene moiety represented by formula (1):

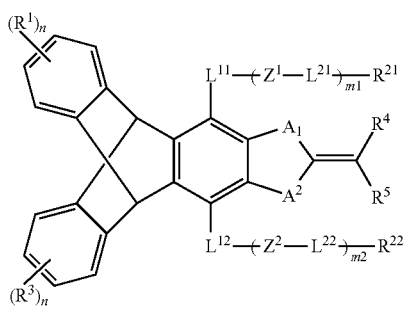

(1)

wherein
$A^1$ and $A^2$ each respectively represent —S—, —O—, —CO—, or —NR—; R represents a hydrogen atom or a substituted or non-substituted alkyl group;

$R^1$ and $R^3$ each respectively represent a substituent selected from the monovalent group consisting of a substituted or non-substituted $C_{1-15}$ linear aliphatic hydrocarbon group, substituted or non-substituted $C_{3-15}$ branched aliphatic hydrocarbon group, substituted or non-substituted $C_{3-15}$ cyclic aliphatic hydrocarbon group, substituted or non-substituted $C_{6-15}$ aryl group, amino group, or a substituent forming by bonding the substituent selected from the monovalent group and one selected from the divalent group consisting of a substituted or non-substituted alkylene group, substituted or non-substituted arylene group, substituted or non-substituted ester group, carbonate ester group, ether group and any combinations of two or more selected from them;

n is an integer from 0 to 2;

$R^4$ and $R^5$ each respectively represent an electron-withdrawing group having a Hammett's substituent constant $\sigma_p$ of equal to or more than 0;

$L^{11}$, $L^{12}$, $L^{21}$ and $L^{22}$ each respectively represent a single bond or a divalent group selected from the group consisting of —O—, —S—, —S(=O)$_2$—, —CO—, —OCO—, —COO—, —OCOO— and —NR$^A$— where $R^A$ represents a $C_{1-7}$ alkyl group or hydrogen atom, —CH$_2$— and any combinations thereof;

$Z^1$ and $Z^2$ each respectively represent a divalent 5- or 6-membered cyclic linking group;

$R^{21}$ and $R^{22}$ each respectively represent a hydrogen atom or substituted or non-substituted alkyl group; and m1 and m2 each respectively represent an integer of from 0 to 2.

[2] The compound of [1], wherein, in formula (1), $Z^1$ and $Z^2$ each respectively represent 1,4-cyclohexylene or 1,4-phenylene.

[3] The compound of [1] or [2], wherein, in formula (1), $A^1$ and $A^2$ are —S—.

[4] The compound of any one of [1]-[3], wherein, in formula (1), m1 and m2 each respectively represent 0 or 1.

[5] The compound of any one of [1]-[4], wherein, in formula (1), $L^{11}$ and $L^{12}$ each respectively represent —OC(=O)— or —C(=O)O—.

[6] The compound of any one of [1]-[5], wherein, in formula (1), $L^{21}$ and $L^{22}$ represent a single bond; and $R^{21}$ and $R^{22}$ each respectively represent a non-substituted alkyl group.

[7] The compound of any one of [1]-[6], wherein, in formula (1), $R^4$ and $R^5$ each respectively represent cyano or —C(=O)O—R' where R' represents a substituted or non-substituted $C_{1-15}$ alkyl group or substituted or non-substituted $C_{6-15}$ aryl group.

According to the invention, it is possible to provide a novel compound having a triptycene moiety useful as a functional material. The compound of the present invention may be used for electroluminescence materials and optical parts such as lenses.

DETAILED DESCRIPTION OF THE INVENTION

The compound having a triptycene moiety of the invention is hereunder described in detail by referring to embodiments. In this specification, a numerical range expressed by the terms "a number to another number" means a range falling between the former number indicating a lower limit value of the range and the latter number indicating an upper limit value thereof.

The present invention relates to the compound, having a triptycene moiety, represented by formula (1)

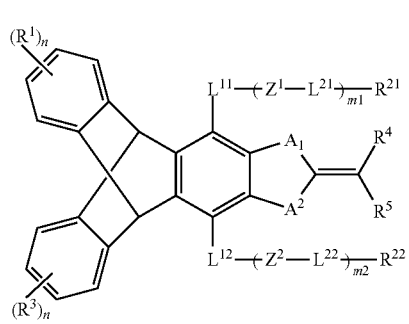

(1)

In the formula, $A^1$ and $A^2$ each respectively represent —S—, —O—, —CO—, or —NR—; R represents a hydrogen atom or a substituted or non-substituted alkyl group;

$R^1$ and $R^3$ each respectively represent a substituent selected from the monovalent group consisting of a substituted or non-substituted $C_{1-15}$ linear aliphatic hydrocarbon group, substituted or non-substituted $C_{3-15}$ branched aliphatic hydrocarbon group, substituted or non-substituted $C_{3-15}$ cyclic aliphatic hydrocarbon group, substituted or non-substituted $C_{6-15}$ aryl group, amino group, or a substituent forming by bonding the substituent selected from the monovalent group and one selected from the divalent group consisting of a substituted or non-substituted alkylene group, substituted or non-substituted arylene group, substituted or non-substituted ester group, carbonate ester group, ether group and any combinations of two or more selected from them;

n is an integer from 0 to 2;

$R^4$ and $R^5$ each respectively represent an electron-withdrawing group having a Hammett's substituent constant $\sigma_p$ value of equal to or more than 0;

$L^{11}$, $L^{12}$, $L^{21}$ and $L^{22}$ each respectively represent a single bond or a divalent group selected from the group consisting of —O—, —S—, —S(=O)$_2$—, —CO—, —OCO—, —COO—, —OCOO— and —NR$^A$— where R$^A$ represents a $C_{1-7}$ alkyl group or hydrogen atom, —CH$_2$— and any combinations thereof;

$Z^1$ and $Z^2$ each respectively represent a divalent 5- or 6-membered cyclic linking group;

$R^{21}$ and $R^{22}$ each respectively represent a hydrogen atom or substituted or non-substituted alkyl group; and m1 and m2 each respectively represent an integer of from 0 to 2.

In formula (1), $A^1$ and $A^2$ each respectively represent —S—, —O—, —CO—, or —NR—, preferably —S—, —O—, —CO—, or —NR—, or more preferably —S—.

In —NR—, R represents a hydrogen atom or a substituted or non-substituted alkyl group (for example, substitute or non-substituted $C_{1-15}$, more preferably $C_{1-10}$, or even more preferably $C_{1-5}$ alkyl group). R may have at least one substituent selected from Substituent Group V described later. R preferably represents a hydrogen atom or non-substituted alkyl group. Examples of —NR— include —NH—, —NCH$_3$— and —NC$_2$H$_5$—.

Preferable examples of the compound represented by formula (1) include the compounds in which $A^1$ and $A^2$ are —S—, or that is, the compounds represented by formula (1a). The definitions of the symbols in formula (1a) are same as those in formula (1) respectively, and their preferable examples are same as those in formula (1) respectively.

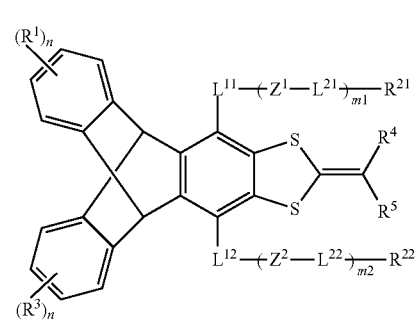

(1a)

In formula (1), $R^1$ and $R^3$ each respectively represent a substituent selected from the monovalent group consisting of a substituted or non-substituted $C_{1-15}$ linear aliphatic hydrocarbon group such as a substituted or non-substituted $C_{1-15}$ linear alkyl group, substituted or non-substituted $C_{3-15}$ branched aliphatic hydrocarbon group such as a substituted or non-substituted $C_{3-15}$ branched alkyl group, substituted or non-substituted $C_{3-15}$ cyclic aliphatic hydrocarbon group, substituted or non-substituted $C_{6-15}$ aryl group (such as phenyl or naphthyl), amino group, or a substituent forming by bonding the substituent selected from the monovalent group and one selected from the divalent group consisting of a substituted or non-substituted alkylene group, substituted or non-substituted arylene group, substituted or non-substituted ester group, carbonate ester group, ether group and any combinations of two or more selected from them. $R^1$ or $R^3$ may have at least one substituent selected from Substituent Group V described later.

Preferably, $R^1$ and $R^3$ each respectively represent a substituted or non-substituted $C_{1-15}$ linear alkyl group, or substituted or non-substituted branched $C_{3-15}$ alkyl group; and more preferably methyl.

In formula (1), $R^4$ and $R^5$ each respectively represent an electron-withdrawing group having a Hammett's substituent value $\sigma_p$ of equal to or more than 0. Preferably, $R^4$ and $R^5$ each respectively represent an electron-withdrawing group having a Hammett's substituent constant $\sigma_p$ value of more than 0; or more preferably, $R^4$ and $R^5$ each respectively represent an electron-withdrawing group having a Hammett's substituent constant $\sigma_p$ value of 0 to 1.5. Examples of such an electron-withdrawing group include trifluoromethyl, cyano, carbonyl, —C(=O)O—R', —C(=O)NH—R', and nitro. R' represents a substituted or non-substituted $C_{1-15}$ linear or branched alkyl group, or substituted or non-substituted $C_{6-15}$ aryl group such as phenyl and naphthyl. Or $R^4$ and $R^5$ may bond to each other to form a ring. Examples of the ring formed by bonding $R^4$ and $R^5$ include the ring shown below. In the formula, "**" indicates the portion linking to the 5-membered ring.

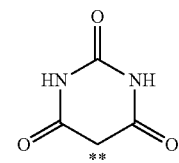

The Hammett's substituent constant $\sigma_p$ and $\sigma_m$ values can be found in many general literatures. For example, such values are described in detail in e.g. "Hammett Rule-Structure and Reactivity-" by Naoki Inamoto (Maruzen), "New Chemical Experiments, Vol. 14, Synthesis and Reaction of Organic Compounds, V", page 2605, edited by the Chemical Society of Japan (Maruzen), "Theoretical Organic Chemistry", page 217, by Tadao Nakatani (Tokyo Kagaku Dojin), and "Chemical Reviews", Vol. 91, pp. 165-195, (1991).

In formula (1), preferably, $R^4$ and $R^5$ each respectively represent cyano, —C(=O)O—R', —C(=O)N—R' or —C(=O)—R'. R' represents a substituted or non-substituted $C_{1-15}$ linear or branched alkyl group, or substituted or non-substituted $C_{6-15}$ aryl group such as phenyl and naphthyl. The number of carbon atoms in the alkyl group is preferably from 1 to 5. The aryl group is preferably phenyl. Especially, at least one of $R^4$ and $R^5$ is cyano. Preferably, another represents cyano or —C(=O)O—R'. Namely, preferable examples of the compound represented by formula (1) include the compounds represented by formula (1b) or (1c). The definitions of the symbols in the formulas are same as those in formula (1) respectively, and their preferable examples are same as those in formula (1) respectively.

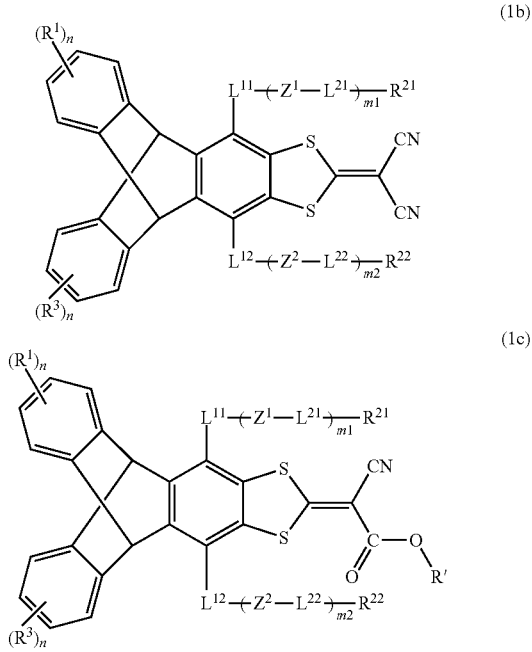

In formula (1c), R' preferably represents a linear or branched $C_{1-10}$ or more preferably $C_{1-5}$ alkyl group or phenyl. The alkyl group or phenyl may have at least one substituent selected from Substituent Group V described later. Among those, hydroxy or alkoxy is preferable. The non-substituted alkyl group or phenyl is also preferable.

In the formula, n is same or different from each other, and represents an integer from 0 to 2, preferably 0 or 1. n=0, that is, no substitution is also preferable.

Preferable examples of the divalent linking group represented by $L^{11}$, $L^{12}$, $L^{21}$ or $L^{22}$ in formula (1) include —C(=O)O—, —OC(=O)—, —OC(=O)O—, —O—, —C(=O)NH—, —NHC(=O)—, —C(=O)N(CH$_3$)—, —N(CH$_3$)C(=O)—, —OC(=O)NH—, —NHC(=O)O—, —NHC(=O)NH—, —C(=O)O(CH$_2$)$_p$O— where p is an integer of equal to or more than 1, or —OCH$_2$—.

In formula (1), preferably, $L^{11}$ and $L^{12}$ each respectively represent a single bond, *—C(=O)O—, *—OC(=O)—, *—C(=O)NH—, *—NHC(=O)—, *—C(=O)N(CH$_3$)—, —N(CH$_3$)C(=O)—, *—O—, *—CH$_2$O—, or *—OCH$_2$—, or more preferably *—C(=O)O— or *—OC(=O)—. It is to be noted that "*" indicates the position linking to the benzene ring.

In formula (1), preferably, $L^{21}$ and $L^{22}$ each respectively represent a single bond, *—O—, *—CH$_2$O—, *—C(=O)O—, *—OC(=O)—, *—NH—, *—NHC(=O)—, *—CH$_2$—NH—, or *—CH$_2$NHC(=O)—, or more preferably a single bond, *—O—, or —OC(=O)O—. It is to be noted that "*" indicates the position linking to $Z^1$ or $Z^2$.

In formula (1), $Z^1$ and $Z^2$ each respectively represent a divalent 5- or 6-membered cyclic linking group. Examples of the divalent 5-membered cyclic linking group include the divalent groups of furan, pyrrole, thiophene, imidazole, pyrazole and triazole. Examples of the divalent 6-membered cyclic linking group include those shown below. The cyclic linking group may have at least one substituent.

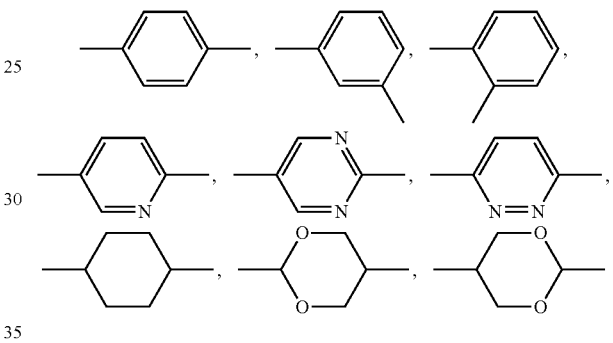

The substituent may be selected from Substituent Group V described below. Substituent Group V:

halogen atoms such as fluorine atom, chlorine atom, bromine atom and iodine atom; linear or branched and substituted or non-substituted alkyls (preferably $C_{1-30}$ alkyls) such as methyl, ethyl, n-propyl, isopropyl, tert-butyl, n-octyl and 2-ethyl hexyl; substituted or non-substituted cycloalkyls (preferably $C_{3-30}$ cycloalkyls) such as cyclohexyl, cyclopentyl and 4-n-dodecyl cyclohexyl; substituted or non-substituted bicycloalkyls (preferably $C_{5-30}$ bicycloalkyls which are residues of $C_{5-30}$ bicycloalkanes without a hydrogen atom) such as bicyclo[1,2,2]heptane-2-yl and bicyclo[2,2,2]octane-3-yl; substituted or non-substituted alkenyls (preferably $C_{2-30}$ alkenyl) such as vinyl and allyl; substituted or non-substituted cycloalkenyls (preferably $C_{3-30}$ cycloalkenyl which are residues $C_{3-30}$ cycloalkens without a hydrogen atom) such as 2-cyclopentene-1-yl and 2-cyclohexene-1-yl; substituted or non-substituted bicycloalkenyls (preferably $C_{5-30}$ bicycloalkenyls which are residues of $C_{5-30}$ bicycloalkenes without a hydrogen atom) such as bicyclo[2,2,1]hepto-2-en-1-yl and bicycl[2,2,2]octo-2-en-4-yl; substituted or non-substituted alkynyls (preferably $C_{2-30}$ alkynyl) such as ethynyl and propargyl; substituted or non-substituted aryls (preferably $C_{6-30}$ aryls) such as phenyl, p-tolyl and naphthyl; substituted or non-substituted heterocyclic group (preferably residues of aromatic or non aromatic 5- or 6-membered hetero-ring compounds without a hydrogen atom; and more preferably residues of aromatic 5- or 6-membered $C_{3-30}$ hetero-ring compounds without a hydrogen atom) such as 2-furyl, 2-thienyl, 2-pyrimidyl, and 2-benzothiazolyl; cyano, hydroxyl, nitro, carboxyl, substituted or non-substituted alkoxys (preferably $C_{1-30}$ alkoxyl) such as methoxy, ethoxy, isopropoxy, tert-butoxy, n-octyloxy and 2-methoxyethoxy; substituted or non-substituted aryloxys (preferably $C_{6-30}$ aryloxys) such as phenoxy, 2-methylphenoxy, 4-tert-butyl phenoxy, 3-nitro phenoxy, and 2-tetradecanoyl aminophenoxy; silyloxys (preferably $C_{3-20}$ silyloxys) such as trimethyl silyloxy and tert-butyl dimethylsilyloxy; substituted or non-substituted heterocyclic oxy group (preferably $C_{2-30}$ heterocyclic oxy group) such as 1-phenyltetrazole-5-oxy and 2-tetrahydro pyranyloxy; substituted or non-substituted acyloxys (preferably formyloxy, $C_{2-30}$ alkylcarbonyloxys and $C_{6-30}$ arylcarbonyloxys) such as formyloxy, acetyloxy, pivaloyloxy, stearoyloxy, benzoyloxy and p-methoxyphenyl carbonyloxy; substituted or non-substituted carbamoyloxys (preferably non-substituted and substituted $C_{1-30}$ alkyl carbamoyloxys) such as N,N-dimethyl carbamoyloxy, N,N-diethyl carbamoyloxy, morpholino carbonyloxy, N,N-di-n-octylamino carbonyloxy and N-n-octyl carbamoyloxy; substituted or non-substituted alkoxycarbonyloxys (preferably $C_{2-30}$ alkoxycarbonyloxys) such as methoxycarbonyloxy, ethoxycarbonyloxy, tert-butoxycarbonyloxy and n-octylcarbonyloxy; substituted or non-substituted aryloxycarbonyloxys (preferably $C_{7-30}$ aryloxycarbonyloxys) such as phenoxycarbonyloxy, p-methoxyphenoxy carbonyloxy and p-n-hexadecyloxy phenoxy carbonyloxy; substituted or non-substituted aminos (preferably amino, $C_{1-30}$ alkylaminos and $C_{6-30}$ anilinos) such as amino, methylamino, dimethylamino, anilino, N-methyl-anilino and diphenyl amino; substituted or non-substituted acylaminos (preferably formylamino, alkylcarbonylaminos and $C_{6-30}$ arylcarbonylaminos) such as formylamino, acetylamino, pivaloylamino, lauroylamino and benzoylamino; substituted or non-substituted aminocarbonylaminos (preferably $C_{1-30}$ aminocarbonylaminos) such as carbamoylamino, N,N-dimethylaminocarbonylamino, N,N-diethylaminocarbonylamino and morpholino carbonylamino; substituted or non-substituted alkoxycarbonylaminos (preferably $C_{2-30}$ alkoxycarbonylaminos) such as methoxy carbonylamino, ethoxycarbonyl amino, tert-butoxycarbonyl amino, n-octadecyloxy carbonylamino and N-methyl-methoxy carbonylamino; substituted or non-substituted aryloxy carbonylaminos (preferably $C_{7-30}$ aryloxy carbonylaminos) such as phenoxy carbonylamino, p-chlorophenoxy carbonylamino and m-n-octyloxyphenoxy carbonylamino; substituted or non-substituted sulfamoylaminos (preferably $C_{0-30}$ sulfamoylaminos) such as sulfamoylamino, N,N-dimethylamino sulfonylamino and N-n-octylamino sulfamoylamino; substituted or non-substitute alkyl- or aryl-sulfonylaminos (preferably $C_{1-30}$ alkyl sulfonylaminos and $C_{6-30}$ aryl sulfonylaminos) such as methyl sulfonylamino, butyl sulfonylamino, phenyl sulfonylamino, 2,3,5-trichlorophenyl sulfonylamino and p-methylphenyl sulfonylamino; mercapto, substituted or non-substituted alkylthios (preferably $C_{1-30}$ alkylthios such as methylthio, ethylthio and n-hexadecylthio; substituted or non-substituted arylthios (preferably $C_{6-30}$ arylthios) such as phenylthio, p-chlorophenylthio and m-methoxy phenylthio; substituted or non-substituted heterocyclic thio group (preferably $C_{2-30}$ heterocyclic thio group) such as 2-benzothiazolylthio and 1-phenyl tetrazole-5-ylthio; substituted or non-substituted sulfamoyls (preferably $C_{0-30}$ sulfamoyls) such as N-ethyl sulfamoyl, N-(3-dodecyloxy propyl)sulfamoyl, N,N-dimethyl sulfamoyl, N-acetyl sulfamoyl, N-benzoyl sulfamoyl and N—(N'-phenyl carbamoyl)sulfamoyl; sulfo, substituted or non-substituted alkyl- or aryl-sulfinyls (preferably $C_{1-30}$ alkyl sulfinyls and $C_{6-30}$ aryl sulfinyls) such as methyl sulfinyl, ethyl sulfinyl, phenyl sulfinyl and p-methylphenyl sulfinyl; substituted or non-substituted alkyl- or aryl-sulfonyls (preferably $C_{1-30}$ alkyl sulfonyls and $C_{6-30}$ aryl sulfonyls) such as methyl sulfonyl, ethyl sulfonyl, phenyl sulfonyl and p-methylphenyl sulfonyl; substituted or non-substituted acyls (preferably formyl, $C_{2-30}$ alkylcarbonyls and $C_{7-30}$ arylcarbonyls) such as formyl, acetyl and pivaloyl benzoyl; substituted or non-substituted aryloxy carbonyls (preferably $C_{7-30}$ aryloxy carbonyls) such as phenoxy carbonyl, o-chlorophenoxy carbonyl, m-nitrophenoxy carbonyl and p-tert-butylphenoxy carbonyl; substituted or non-substituted alkoxycarbonyls (preferably $C_{2-30}$ alkoxycarbonyls) such as methoxy carbonyl, ethoxy carbonyl, tert-butoxy carbonyl and n-octadecyloxy carbonyl; substituted or non-substituted carbamoyls (preferably $C_{1-30}$ carbamoyls) such as carbamoyl, N-methyl carbamoyl, N,N-dimethyl carbamoyl, N,N-di-n-octyl carbamoyl and N-(methylsulfonyl) carbamoyl; substituted or non-substituted aryl- or heterocyclic azo group (preferably $C_{6-30}$ aryl azo group and $C_{3-30}$ heterocyclic azo group) such as phenyl azo, p-chlorophenyl azo and 5-ethylthio-1,3,4-thiaziazole-2-yl azo; imido group such as N-succinimido and N-phthalimido; substituted or non-substituted phosphinos (preferably $C_{2-30}$ phosphinos) such as dimethyl phosphino, diphenyl phosphino and methylphenoxy phosphino; substituted or non-substituted phosphinyls (preferably $C_{2-30}$ phosphinyls) such as phosphinyl, dioctyloxy phosphinyl and diethoxy phosphinyl; substituted or non-substituted phosphinyloxys (preferably $C_{2-30}$ phosphinyloxys) such as diphenoxy phosphinyloxy and dioctyloxy phosphinyloxy; substituted or non-substituted phosphinylaminos (preferably $C_{2-30}$ phosphinylaminos) such as dimethoxyphosphinyl amino and dimethylamino phosphinyl amino; and substituted or non-substituted silyls (preferably $C_{3-30}$ silyls) such as trimethyl silyl, tert-butyldimethyl silyl and phenyldimethyl silyl.

The substituents, which have at least one hydrogen atom, may be substituted by at least one substituent selected from these. Examples such substituent include alkylcarbonylaminosulfo, arylcarbonylaminosulfo, alkylsulfonylaminocarbonyl and arylsulfonylaminocarbonyl. More specifically, methylsulfonylaminocarbonyl, p-methylphenylsulfonylaminocarbonyl, acetylaminosulfonyl and benzoylaminosulfonyl are exemplified.

There may be two or more substituents, and they may be same or different from each other. If possible, two or more substituents may bond each other to form a ring.

In formula (1), preferably, $Z^1$ and $Z^2$ each respectively represent 1,4-cyclohexyl or 1,4-phenylene.

There are cis-trans stereoisomers of a cyclohexane ring. According to the invention, the cyclohexane ring may be the mixture of the cis-trans stereoisomers. Preferably, trans-cyclohexane ring.

In formula (1), $R^{21}$ and $R^{22}$ each respectively represent a hydrogen atom or substituted or non-substituted alkyl group. The alkyl group is preferably a $C_{1-30}$ alkyl group such as methyl, ethyl, n-propyl, isopropyl, n-butyl, tert-butyl, n-pentyl, n-hexyl, n-octyl and 2-ethylhexyl. A $C_{1-8}$ alkyl group is more preferable.

In formula (1), m1 and m2 each respectively represent an integer of from 0 to 2, or preferably 0 or 1.

Examples of the compound represented by formula (1) include the compounds represented by formula (1d), (1e) or (1f). The definitions of the symbols in the formulas are same as those in formula (1) respectively, and their preferable examples are same as those in formula (1) respectively.

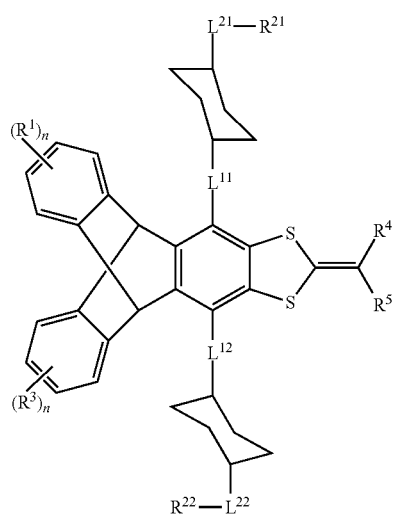

(1d)

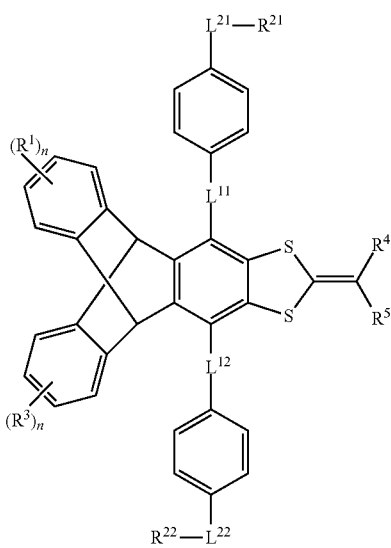

(1e)

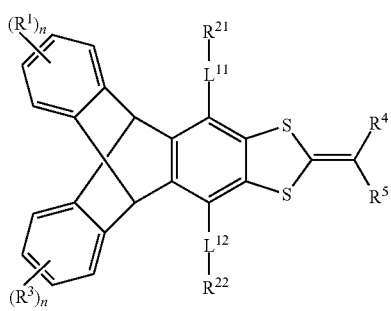

(1f)

Specific examples of the compound represented by formula (1) include those shown below. Regarding the following compounds, they are specified by the number in parentheses, for example "Compound (X)", unless there is another indication.

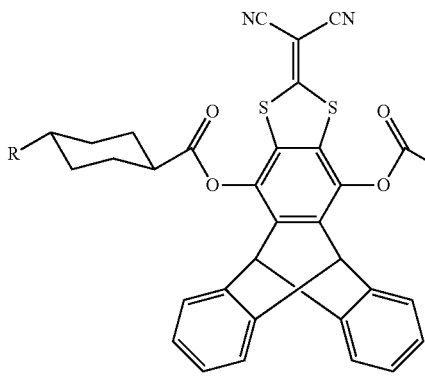

R = —$C_5H_{11}$ (1)
—$C_4H_9$ (2)
—$C_3H_7$ (3)
—$C_2H_5$ (4)

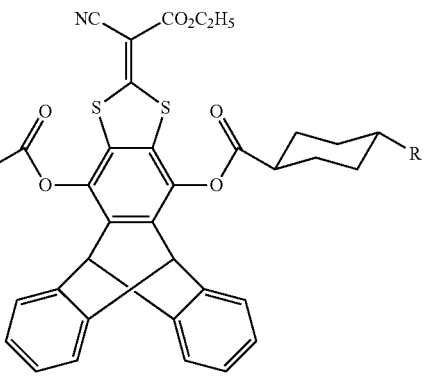

R = —$C_5H_{11}$ (5)
—$C_4H_9$ (6)
—$C_3H_7$ (7)
—$C_2H_5$ (8)

-continued
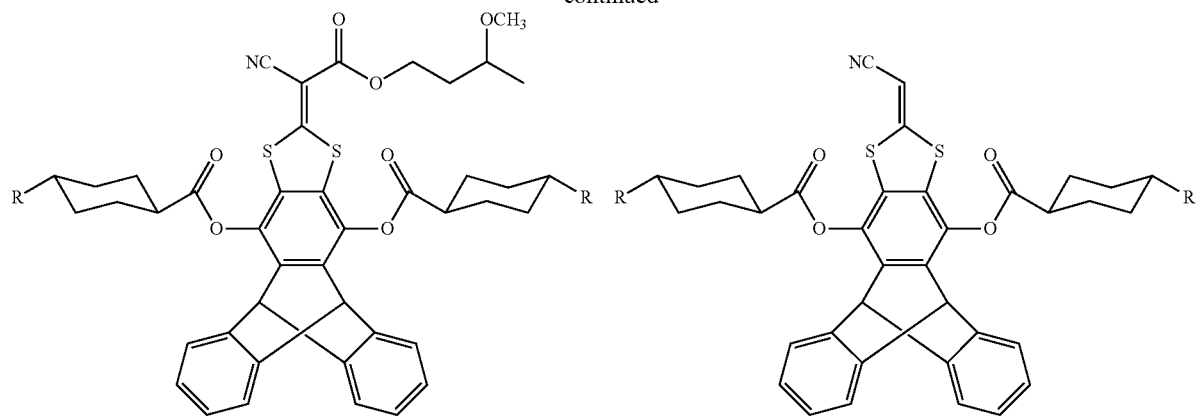
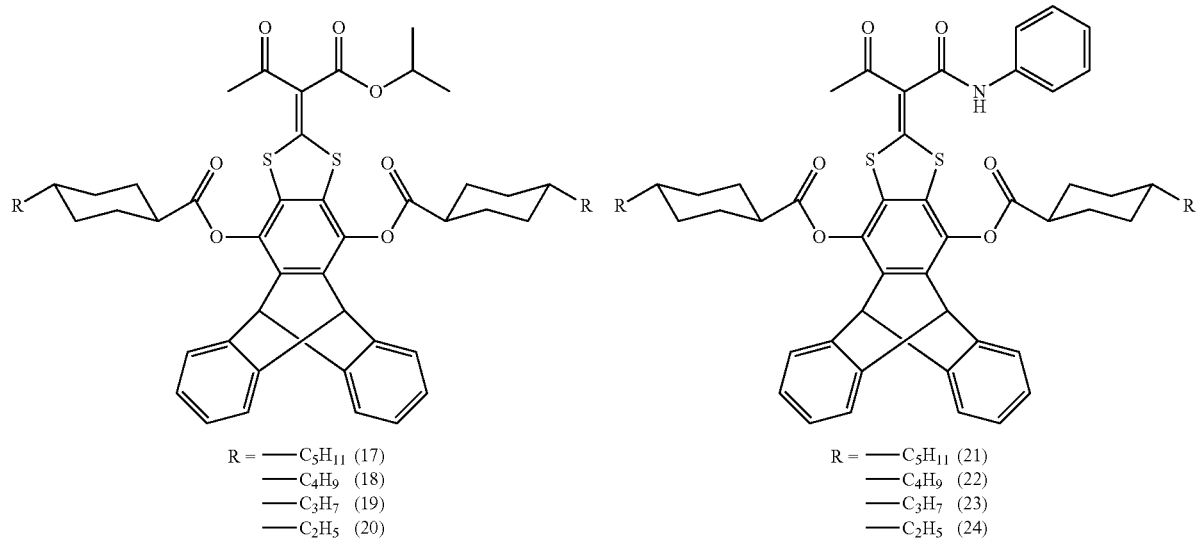
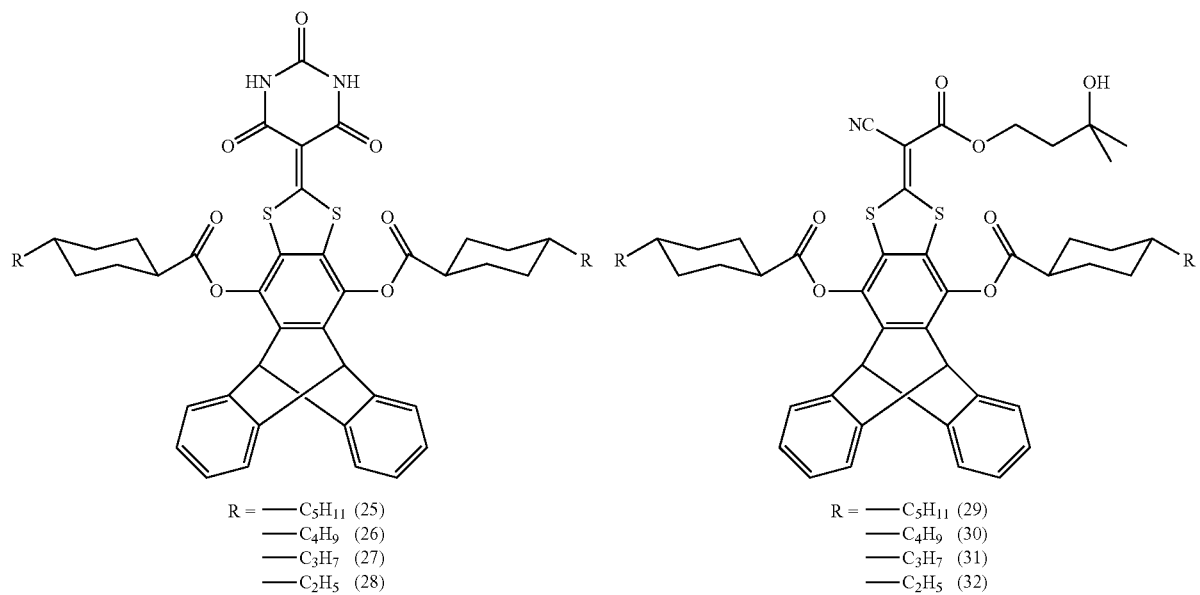

13
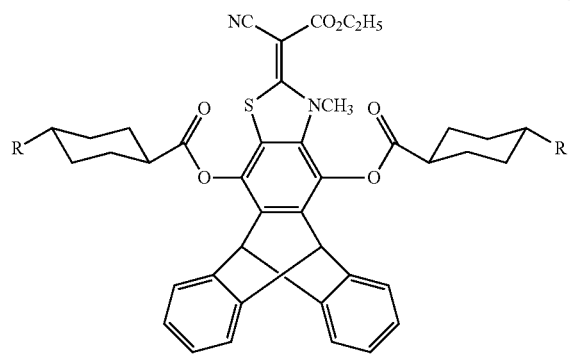
R = —C₅H₁₁ (33)
—C₄H₉ (34)
—C₃H₇ (35)
—C₂H₅ (36)
14
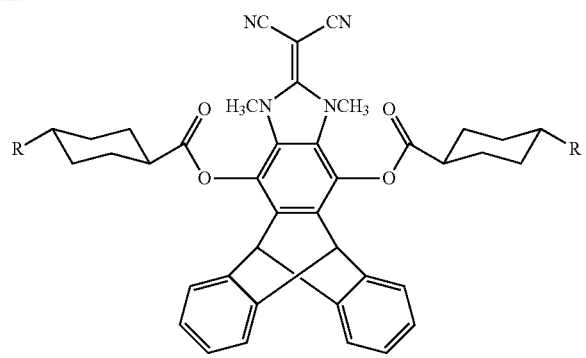
R = —C₅H₁₁ (37)
—C₄H₉ (38)
—C₃H₇ (39)
—C₂H₅ (40)
-continued
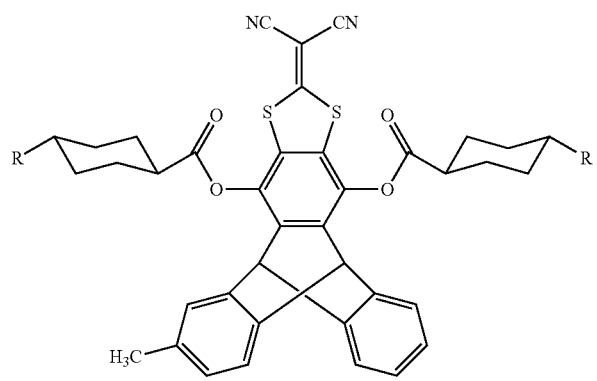
R = —C₅H₁₁ (41)
—C₄H₉ (42)
—C₃H₇ (43)
—C₂H₅ (44)
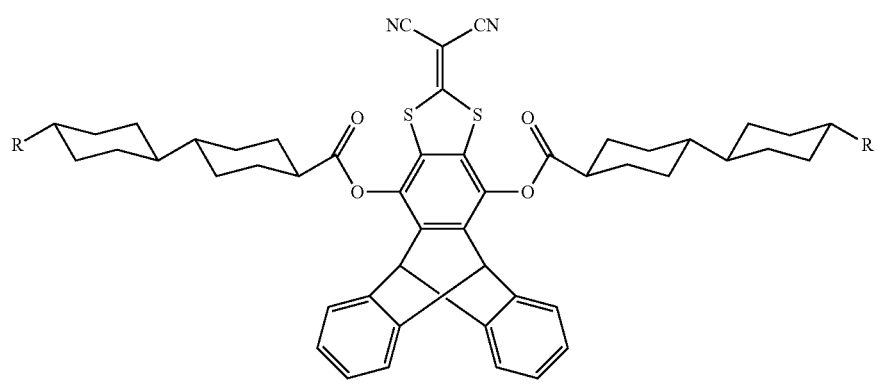
R = —C₅H₁₁ (45)
—C₄H₉ (46)
—C₃H₇ (47)
—C₂H₅ (48)

-continued
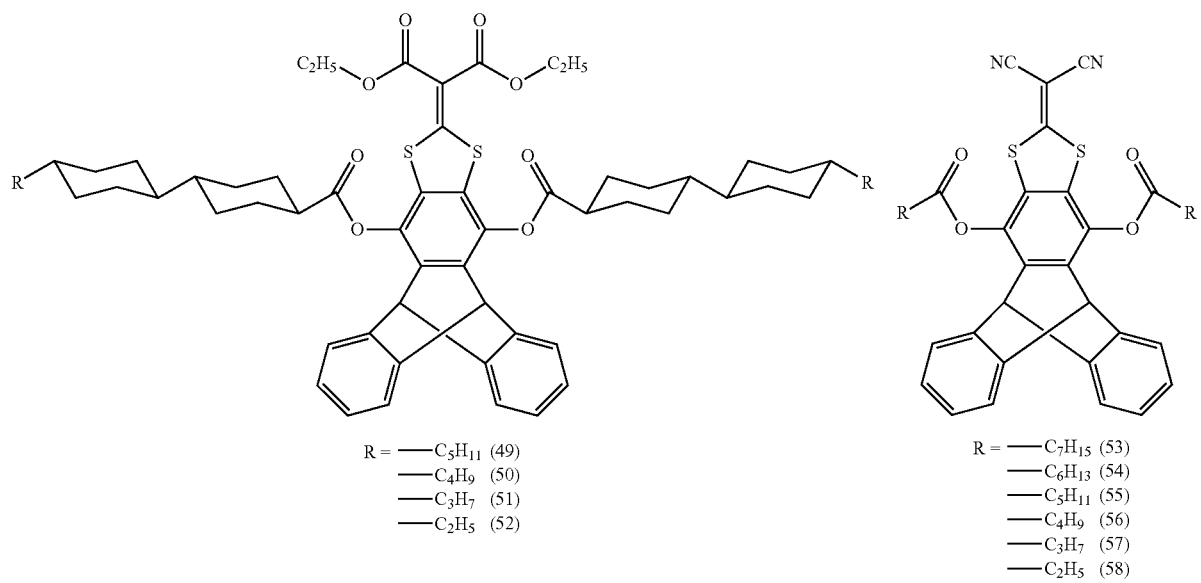
R = —C$_5$H$_{11}$ (49)
—C$_4$H$_9$ (50)
—C$_3$H$_7$ (51)
—C$_2$H$_5$ (52)
R = —C$_7$H$_{15}$ (53)
—C$_6$H$_{13}$ (54)
—C$_5$H$_{11}$ (55)
—C$_4$H$_9$ (56)
—C$_3$H$_7$ (57)
—C$_2$H$_5$ (58)
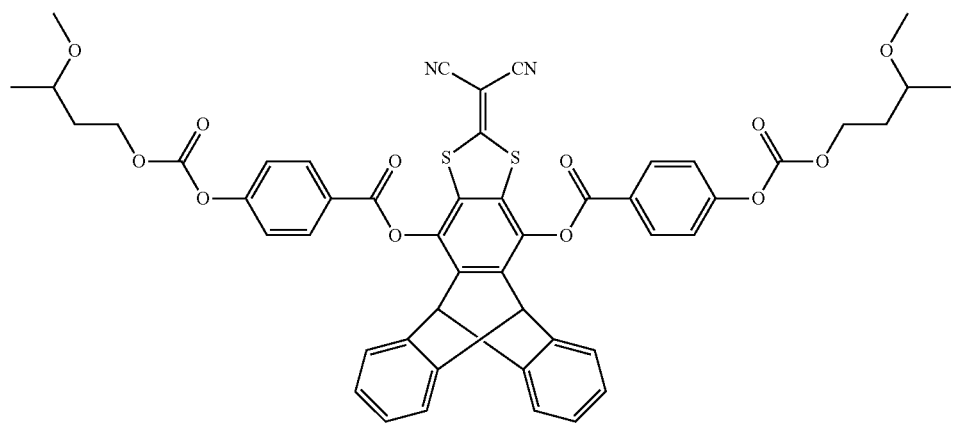
(59)
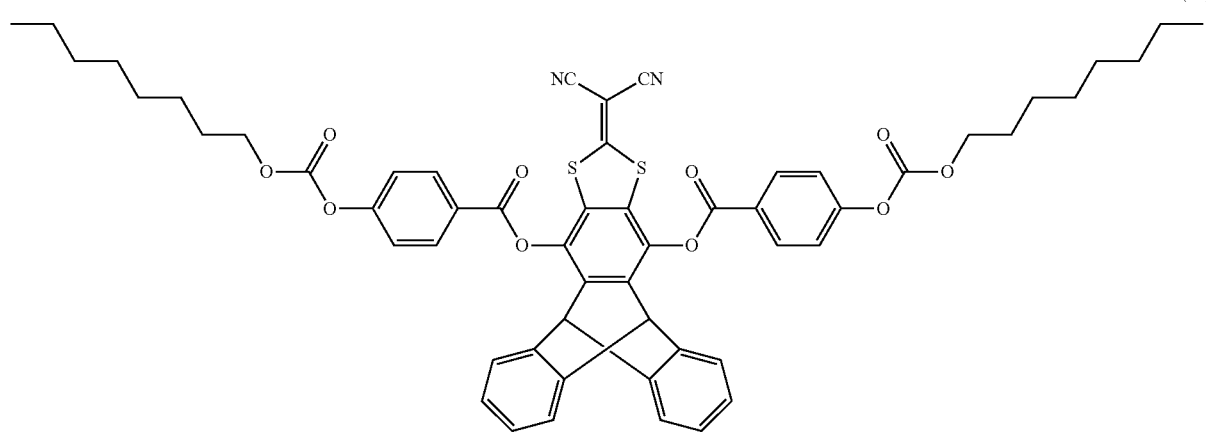
(60)

-continued
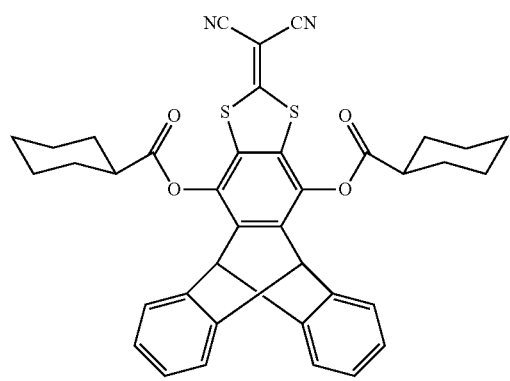
(61)
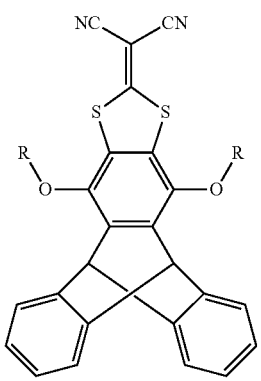
R = —C7H15 (62)
—C6H13 (63)
—C5H11 (64)
—C4H9 (65)
—C3H7 (66)
—C2H5 (67)
—CH3 (68)
—H (69)
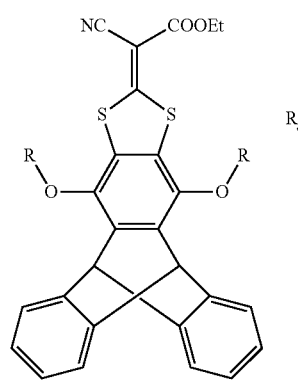
R = —C7H15 (70)
—C6H13 (71)
—C5H11 (72)
—C4H9 (73)
—C3H7 (74)
—C2H5 (75)
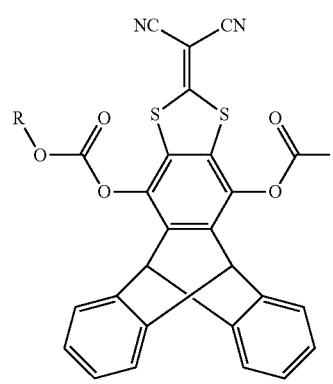
R = —C7H15 (76)
—C6H13 (77)
—C5H11 (78)
—C4H9 (79)
—C3H7 (80)
—C2H5 (81)
—CH3 (82)
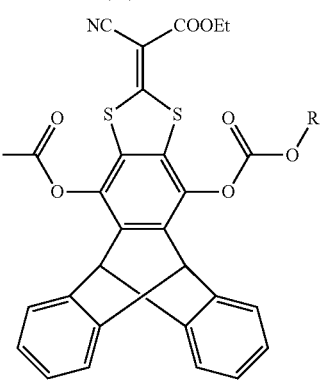
R = —C7H15 (83)
—C6H13 (84)
—C5H11 (85)
—C4H9 (86)
—C3H7 (87)
—C2H5 (88)
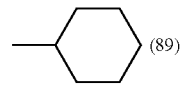 (89)
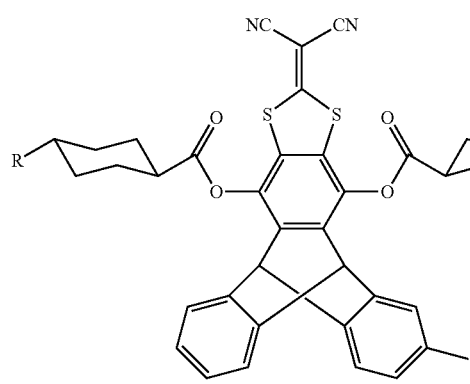
R = —C5H11 (90)
—C4H9 (91)
—C3H7 (92)
—C2H5 (93)
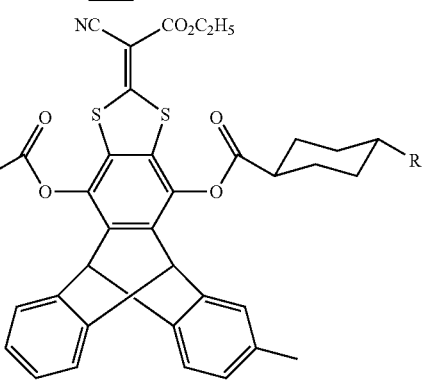
R = —C5H11 (94)
—C4H9 (95)
—C3H7 (96)
—C2H5 (97)

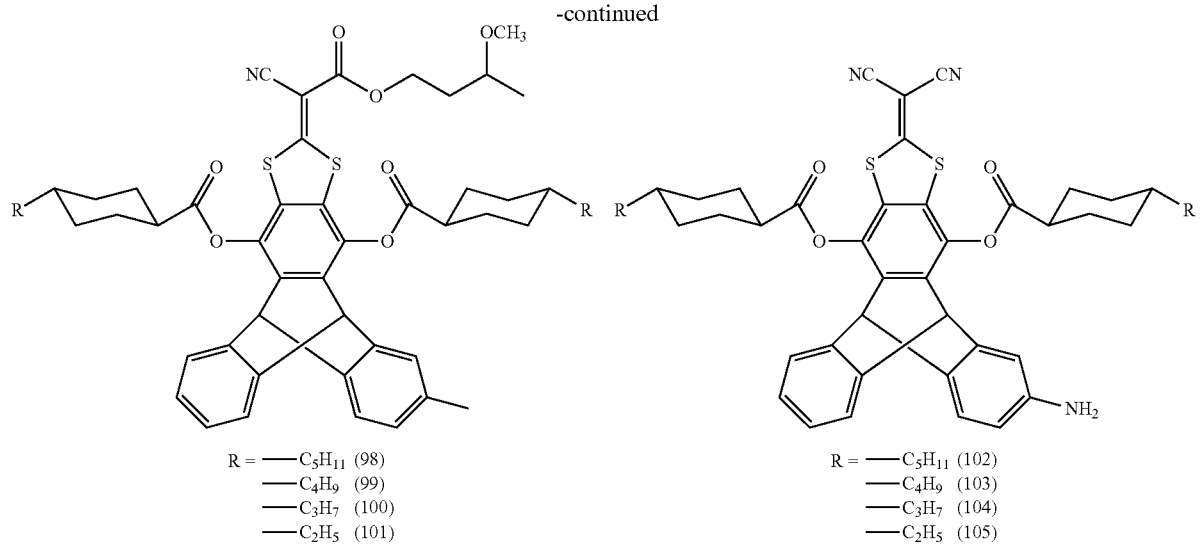

R = —C₅H₁₁ (98)
—C₄H₉ (99)
—C₃H₇ (100)
—C₂H₅ (101)

R = —C₅H₁₁ (102)
—C₄H₉ (103)
—C₃H₇ (104)
—C₂H₅ (105)

The compound represented by formula (1) may be prepared by combining two or more organic synthesis reactions. One example of the method for preparing the compound represented by formula (1), wherein $A^1$ and $A^2$ are —S—, and $R^4$ and $R^5$ are cyano, is as follows. First, compound (1-E) is prepared from compound (1-A) according to the scheme shown below, and then is reacted with arbitrary reagent. The details about the synthesis of compound (1-B) from compound (1-A) are described in "Journal of Organic Chemistry" (2005); 70(3); p. 917-924. The details of the synthesis of compound (1-E) from compound (1-B) are described in "Journal of Chemical Crystallography" (1997); 27(9); p. 515-526.

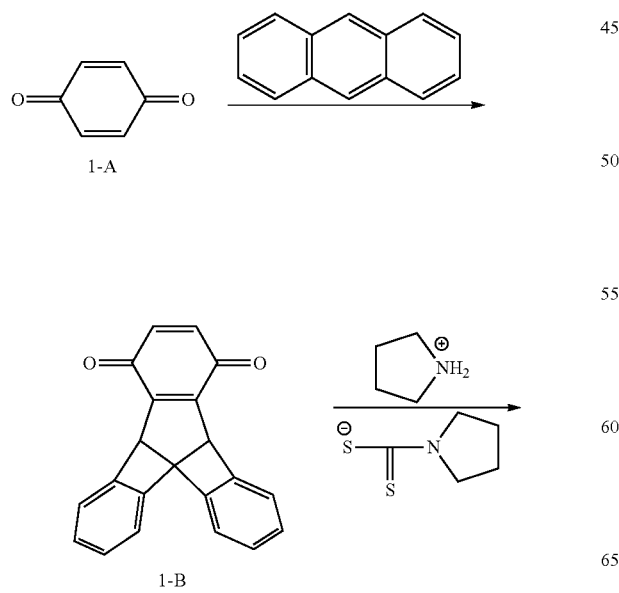

1-A

1-B

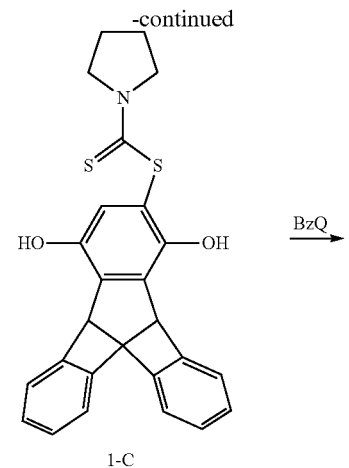

1-C

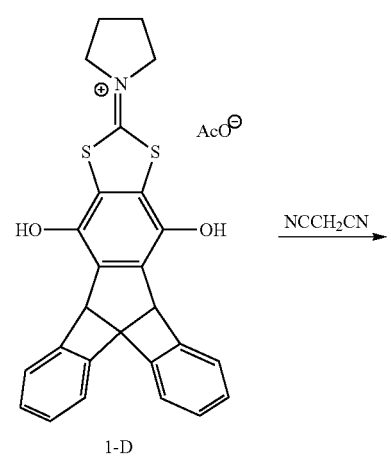

1-D

-continued

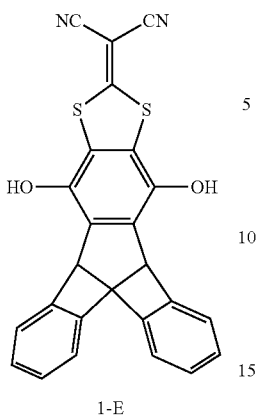

1-E

The compound represented by formula (1), wherein $L^{11}$ and $L^{12}$ are —OCO—, may be prepared by carrying out esterification of compound (1-E) and arbitrary carboxylic acid reagent. After that, further modification may be carried out to give the compound represented by formula (1).

The compound represented by formula (1), wherein $A^1$ and $A^2$ are —S—, $R^4$ is cyano, and $R^5$ is —C(=O)O—R', may be prepared as follows. First, compound (1-D) is prepared from compound (1-A), then is reacted with arbitrary reagent D to give compound (2-D), and then is reacted with arbitrary reagent.

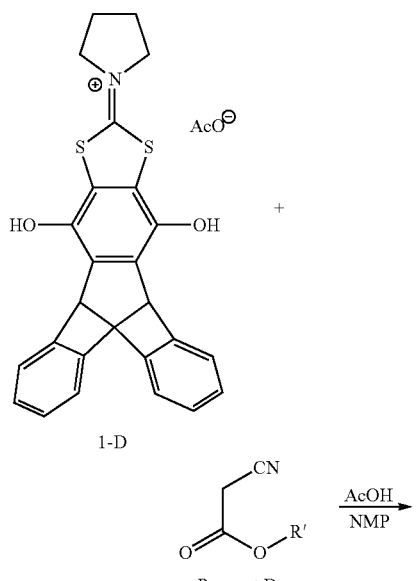

1-D

-continued

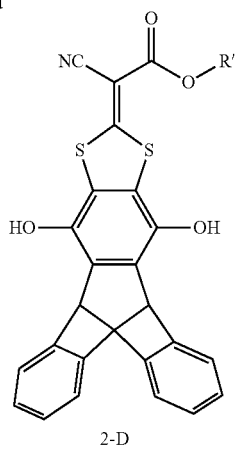

2-D

The compound represented by formula (1), wherein $L^{11}$ and $L^{12}$ are —OCO—, may be prepared by carrying out esterification of compound (2-D) and arbitrary carboxylic acid reagent. After that, further modification may be carried out to give the compound represented by formula (1).

The compound having a triptycene moiety represented by formula (1) may be used in various applications, in which the triptycene compounds have been used previously. For example, the compound of the present invention is useful in various applications of functional materials such as electroluminescence materials, light-waveguides, optical filters, optical parts including lenses, light-emitting devices, electricity or electron materials such as semiconductors and photoresist materials.

Especially, the compound of the invention is expected to be improved in terms of heat-resistance since the compound has a high melting point by having the condensed 5-membered ring

EXAMPLES

The present invention will be explained to further detail, referring to Examples. Note that the materials, reagents, amounts and ratios of substances, operations and so forth explained in Examples below may appropriately be modified without departing from the spirit of the present invention. The scope of the present invention is, therefore, not limited to the specific examples described below.

Example 1

Synthetic Example of Compound (1)

Compound (1) was prepared according to the following scheme.

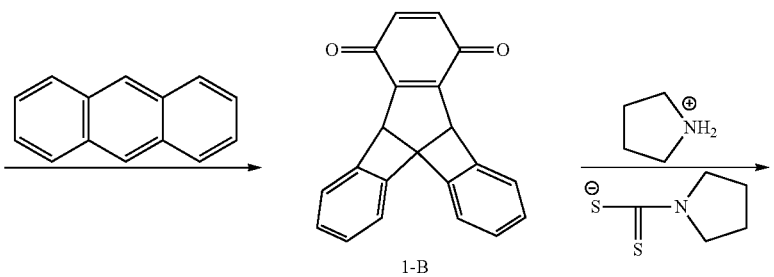

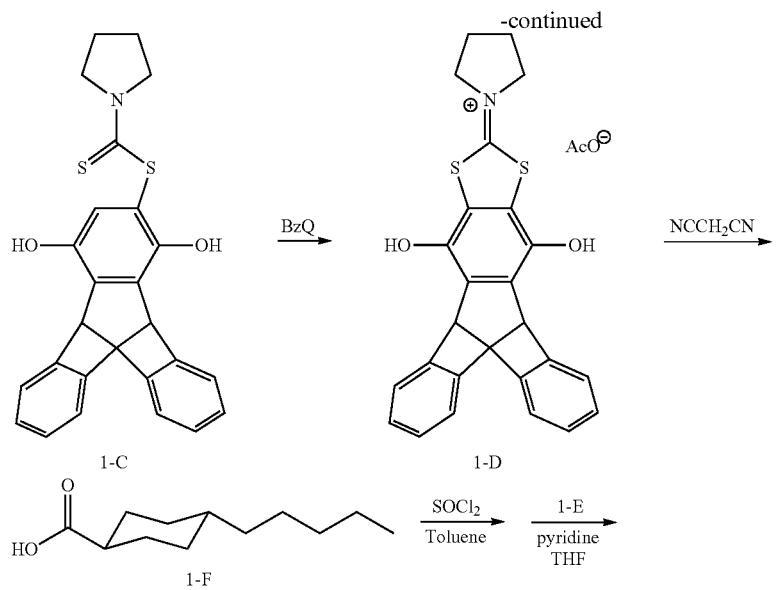

1-C

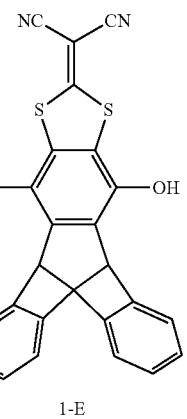

1-D

1-E

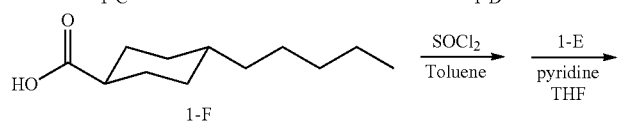

1-F

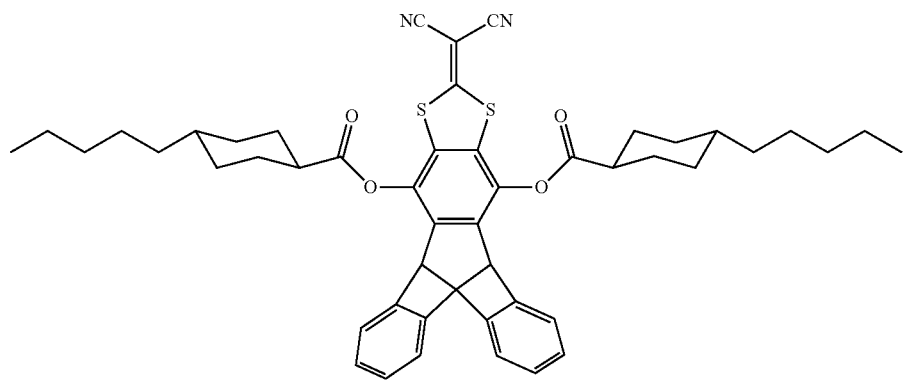

Compound (1)

The synthesis of compound (1-B) from compound (1-A) was carried out according to the method described in "Journal of Organic Chemistry" (2005); 70(3); p. 917-924. The synthesis of compound (1-E) from compound (1-B) was carried out according to the method described in "Journal of Chemical Crystallography" (1997); 27(9); p. 515-526.

Thionyl chloride (0.6 mL, 6.5 mmol) was added to toluene solution (10 mL) of compound (1-F) (1.1 g, 5.4 mmol), and refluxed under heat. After confirming the consumption of the carboxylic acid by TLC, the solvent was evaporated from the reaction solution. The resultant was added dropwise to tetrahydrofuran solution (50 mL) of compound (1-E) (1 g, 2.3 mmol) and pyridine (0.57 mL, 7.1 mmol) under cooling with ices. After the termination of reaction, the resultant was poured into a 300 mL of methanol and then filtered. The obtained solid was dissolved in methylene chloride, and then purified by silica-gel chromatography with methylene chloride as eluent to give 1.4 g of Compound (1) in 75% yield.

The NMR spectral data of Compound (1) are as follows.

$^1$H-NMR (solvent:CDCl$_3$, standard:tetramethylsilane) δ (ppm): 0.90 (6H, t), 1.00-1.20 (4H, m), 1.20-1.40 (18H, m), 1.65-1.80 (4H, m), 1.95-2.05 (4H, m), 2.25-2.35 (4H, m), 2.70-2.80 (2H, m), 5.30 (2H, s), 7.00-7.10 (4H, m), 7.30-7.40 (4H, m).

Example 2

Synthetic Example of Compound (2)

Compound (2) was prepared according to the following scheme.

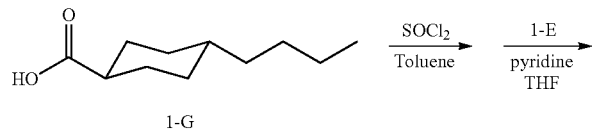

1-G

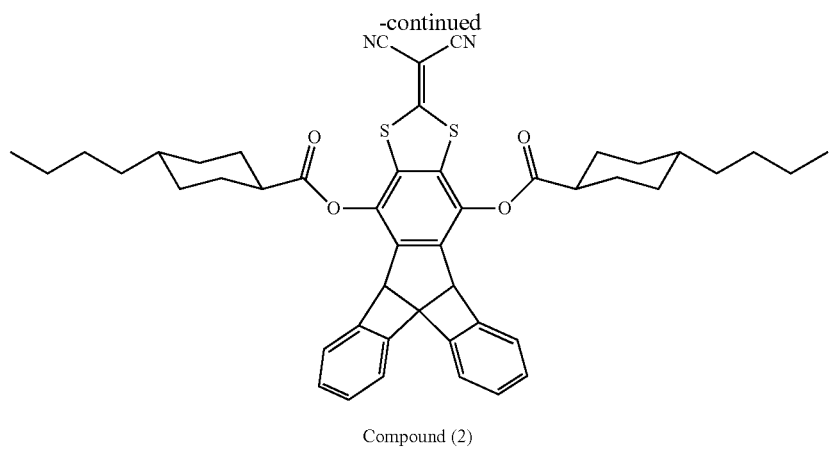

Compound (2)

The synthesis was carried out according to the same manner as Example 1, except that compound (1-F) was replaced with compound (1-G), to give 1.7 g of Compound (2).

The NMR spectral data of Compound (2) are as follows.

$^1$H-NMR (solvent:CDCl$_3$, standard:tetramethylsilane) δ (ppm): 0.90 (6H, t), 1.00-1.20 (4H, m), 1.20-1.40 (14H, m), 1.65-1.80 (4H, m), 1.95-2.05 (4H, m), 2.25-2.35 (4H, m), 2.70-2.80 (2H, m), 5.30 (2H, s), 7.00-7.10 (4H, m), 7.30-7.40 (4H, m).

Example 3

Synthetic Example of Compound (9)

Compound (9) was prepared according to the following scheme.

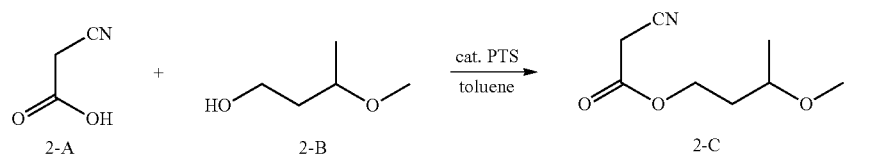

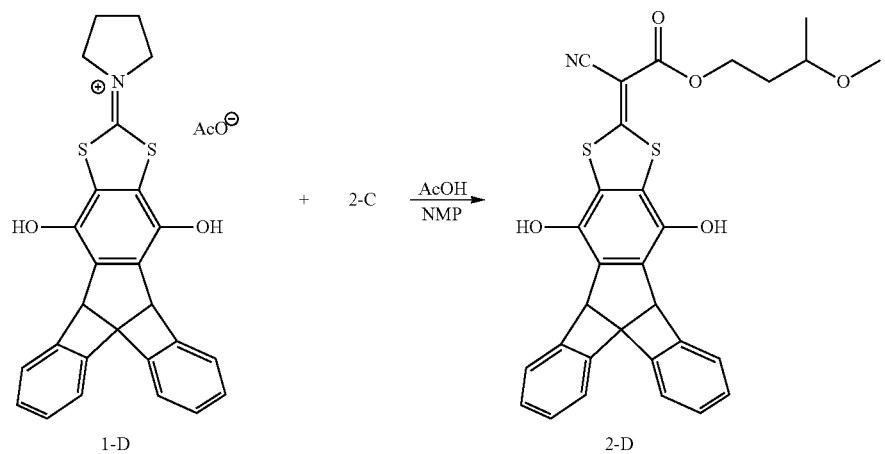

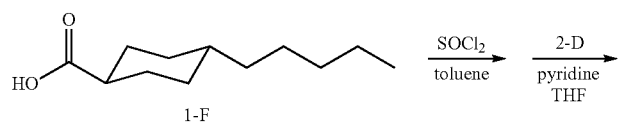

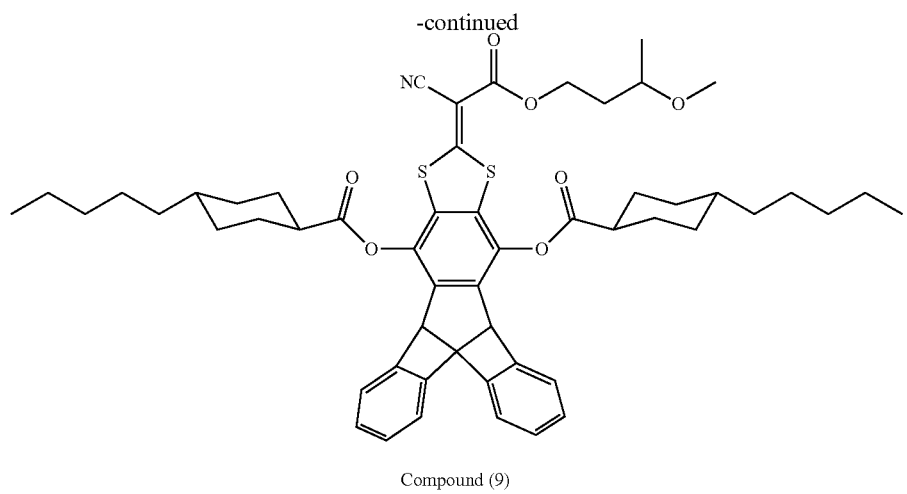

Compound (9)

Para-toluenesulfonic acid, PTS, (0.2 g) was added to a toluene solution (200 mL) of compound (2-A) (37 g, 0.44 mmol) and 2-methoxy butanol (2-B) (46 g, 0.44 mol), and dehydrated during refluxing with Dean-Stark. After the termination of the reaction, toluene was evaporated from the resultant solution. The resultant was cooled by the room temperature, and extracted by adding ethyl acetate and water. The obtained organic layer was washed by adding water, saturated aqueous solution of sodium hydrogen carbonate, 1N-hydrochloric and water in sequence. The organic layer was dried by adding magnesium sulfate, and, after evaporation of the solvent under the reduced pressure, 65 g of the crude product, compound (2-C), was obtained.

The crude product of compound (2-C) (6.5 g) was added to N-methylpyrrolidone (NMP) (80 mL) solution of compound (1-D) (10 g) and stirred at an inner temperature of 120 degrees Celsius for two hours. After cooling, the reaction solution was poured into 1N-hydrochloric acid (300 mL) during being cooled with ices. The obtained solid was filtered and dried. The solid was dispersed into a mixed solvent of acetone/hexane, and then filtered, and then dispersion and filtration were repeated again. The solid was recrystallized in acetic acid (AcOH), filtered and dried to give 90 g of compound (2-D).

Thionyl chloride (0.6 mL, 6.5 mmol) was added to toluene solution (10 mL) of compound (1-F) (1.1 g, 5.4 mmol), and refluxed under heat. After confirming the consumption of the carboxylic acid by TLC, the solvent was evaporated from the reaction solution. The resultant was added dropwise to tetrahydrofuran solution (50 mL) of compound (2-D) (1.2 g, 2.3 mmol) and pyridine (0.57 mL, 7.1 mmol) under cooling with ices. After the termination of reaction, the resultant was poured into a 300 mL of methanol and then filtered. The obtained solid was dissolved in methylene chloride, and then purified by silica-gel chromatography with methylene chloride as eluent to give 1.5 g of Compound (9) in 84% yield. The product was determined by the mass spectroscopy analysis.

Example 4

Synthetic Example of Compound (29)

Compound (29) was prepared according to the following scheme.

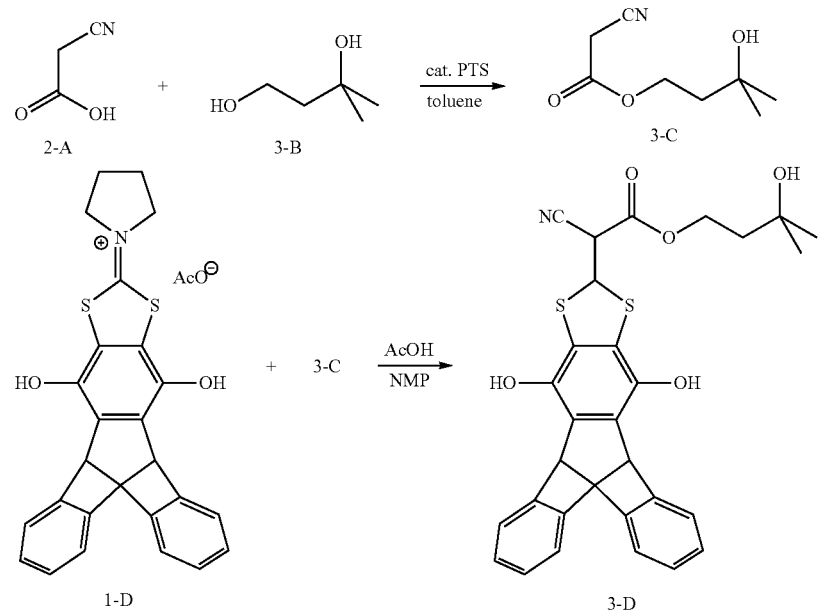

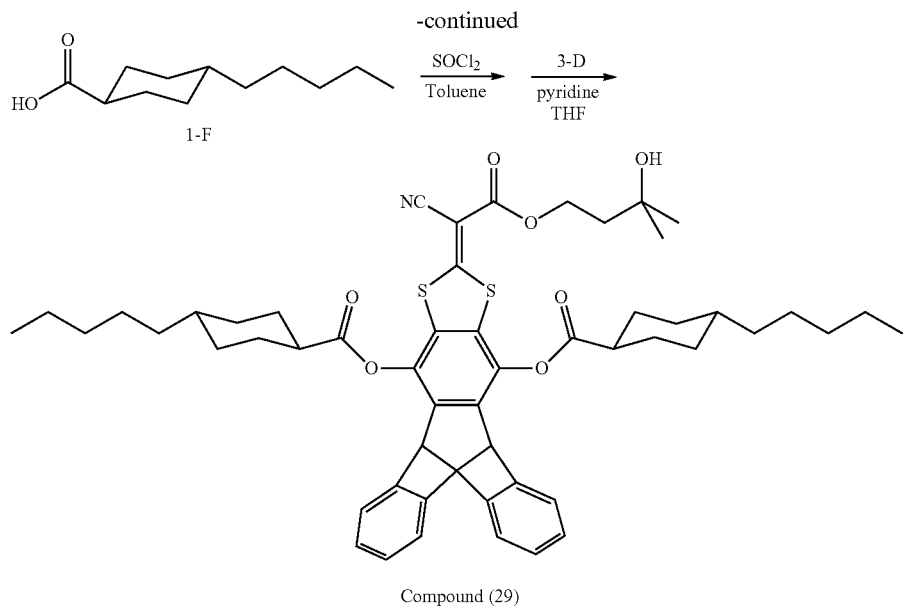

Compound (29)

In the same manner as Example 3, 1.9 g of Compound (29) was prepared, except that the reagents were replaced with those as shown above. The product was determined by the mass spectroscopy analysis.

Example 5

Synthetic Example of Compound (53)

Compound (53) was prepared according to the following scheme.

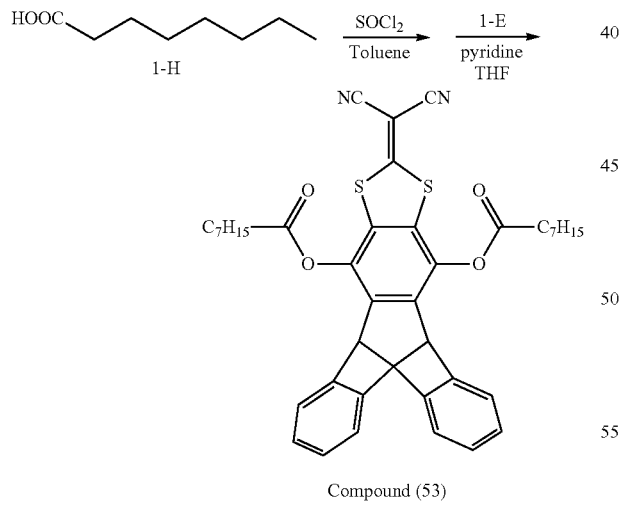

Compound (53)

In the same manner as Example 1, 1.7 g of Compound (53) was prepared, except that compound (1-F) was replaced with compound (1-H).

The NMR spectral data of Compound (53) are as follows.

$^1$H-NMR (solvent:CDCl$_3$, standard:tetramethylsilane) δ (ppm): 0.90 (6H, t), 1.30-1.50 (16H, m), 1.85-2.00 (4H, m), 2.80 (4H, t), 5.30 (2H, s), 7.00-7.10 (4H, m), 7.30-7.40 (4H, m).

Example 6

Synthetic Example of Compound (59)

Compound (59) was prepared according to the following scheme.

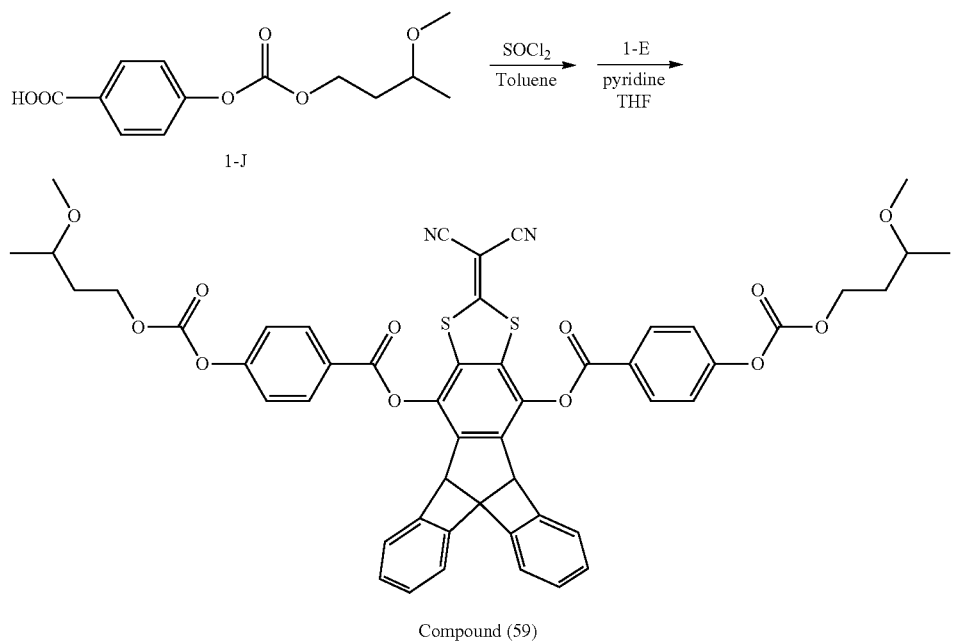

In the same manner as Example 1, 2.1 g of Compound (59) was prepared, except that compound (1-F) was replaced with compound (1-J).

The NMR spectral data of Compound (59) are as follows.

$^1$H-NMR (solvent:CDCl$_3$, standard:tetramethylsilane) δ (ppm): 1.25 (6H, d), 1.90-2.00 (4H, m), 3.40 (6H, s), 3.60 (2H, m), 4.40-4.50 (4H, m), 7.00-7.10 (4H, m), 7.30-7.40 (4H, m), 7.50 (4H, d), 8.40 (4H, d).

Example 7

Synthetic Example of Compound (60)

Compound (60) was prepared according to the following scheme.

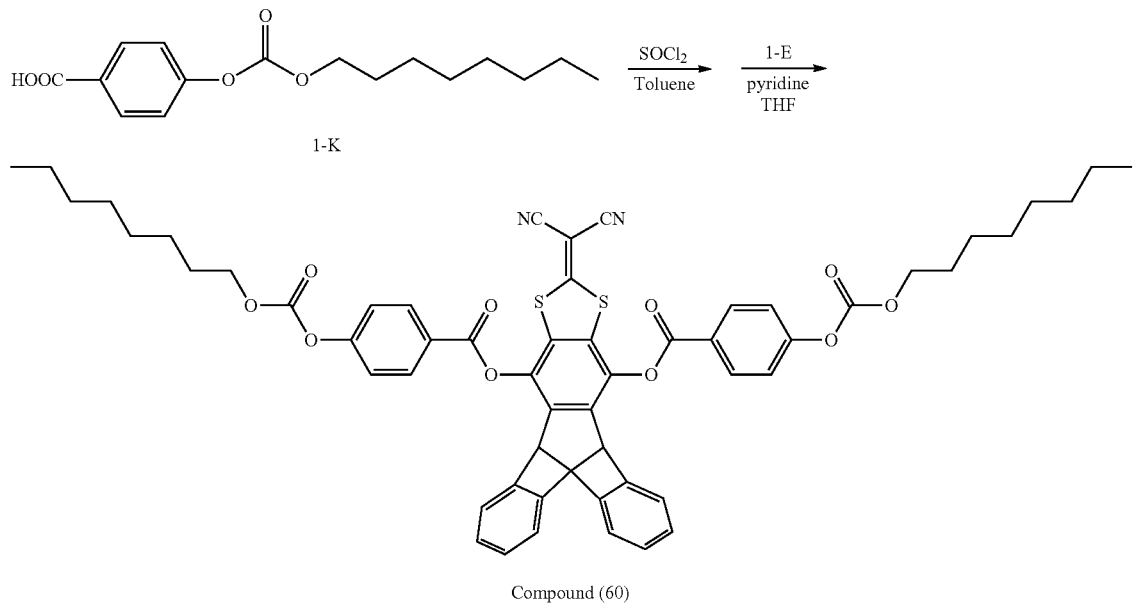

In the same manner as Example 1, 1.5 g of Compound (60) was prepared, except that compound (1-F) was replaced with compound (1-K).

The NMR spectral data of Compound (60) are as follows.

$^1$H-NMR (solvent:CDCl$_3$, standard:tetramethylsilane) δ (ppm): 0.90 (6H, t), 1.25-1.50 (20H, m), 1.75-1.85 (4H, m), 4.35 (4H, t), 5.40 (2H, s), 7.00-7.10 (4H, m), 7.50 (4H, m), 8.40 (4H, m).

Example 8

Synthetic Example of Compound (61)

Compound (61) was prepared according to the following scheme.

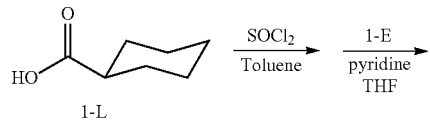

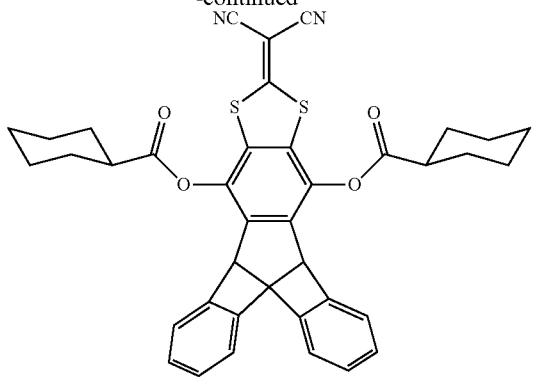

Compound (61)

In the same manner as Example 1, 0.9 g of Compound (61) was prepared, except that compound (1-F) was replaced with compound (1-L).

The NMR spectral data of Compound (61) are as follows.

$^1$H-NMR (solvent:CDCl$_3$, standard:tetramethylsilane) δ (ppm): 1.40-1.60 (8H, m), 1.70-1.80 (4H, m), 1.90-2.00 (4H, m), 2.20-2.30 (4H, m), 2.80-2.90 (2H, m), 5.30 (2H, s), 7.00-7.10 (4H, m), 7.30-7.40 (4H, m).

Example 9

Synthetic Example of Compound (69)

The synthesis was carried out in the same manner as Example 1 to give 7.0 g of Compound (69).

The NMR spectral data of Compound (61) are as follows.

$^1$H-NMR (solvent:CDCl$_3$, standard:tetramethylsilane) δ (ppm): 6.00 (2H, s), 7.00-7.10 (4H, m), 7.40-7.50 (4H, m), 10.40 (H, s).

Example 9

Synthetic Example of Compound (90)

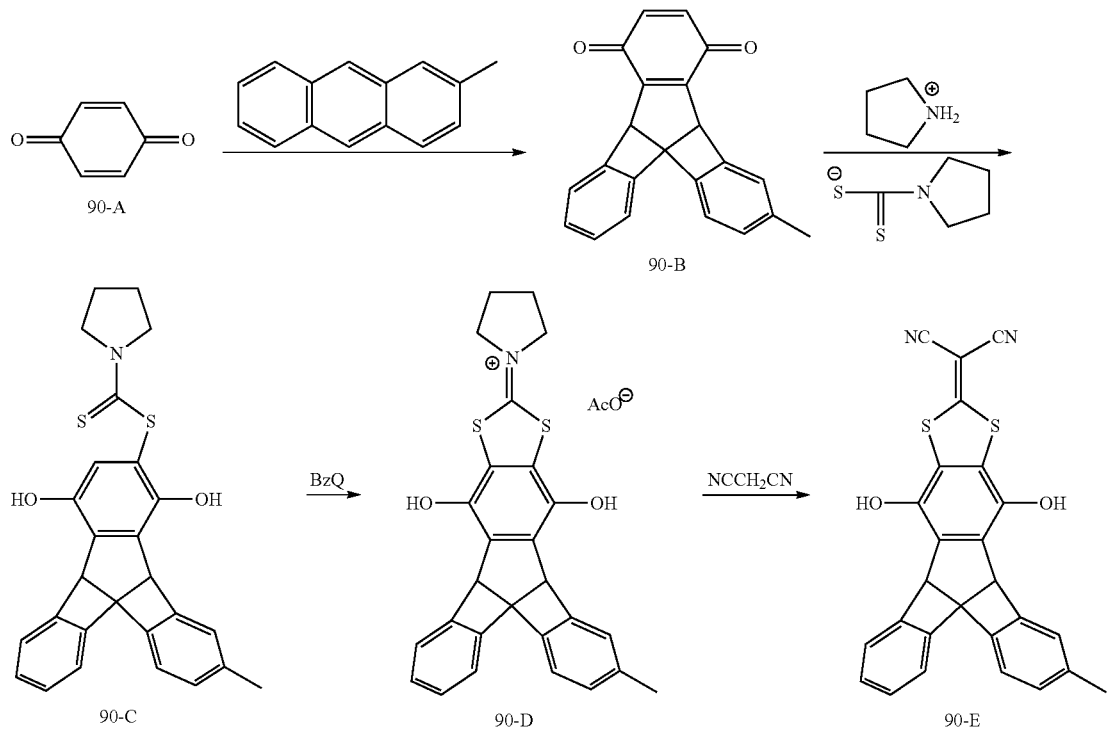

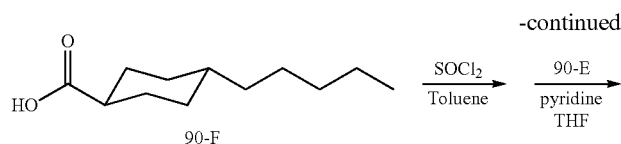

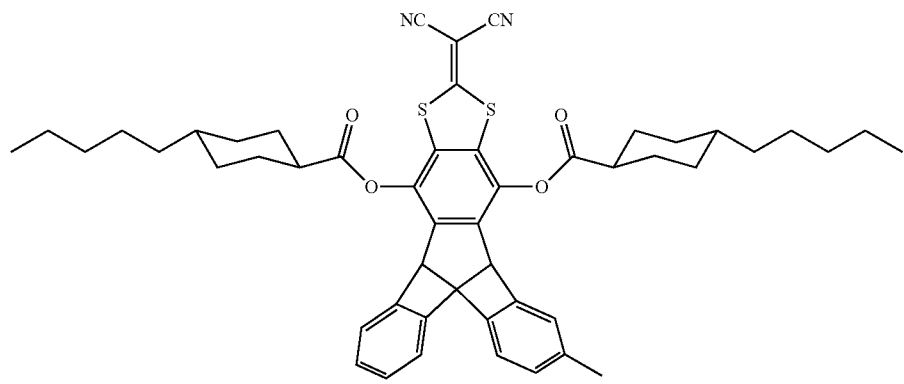

Compound (90)

In the same manner as Example 1, 5.1 g of Compound (90) was prepared, except that the starting material was replaced with 2-methyl anthracene.

The NMR spectral data of Compound (90) are as follows. The product was determined by the mass spectroscopy analysis.

Example 11

Each of the compounds was subjected to a heat-resistance test using a hot-plate, and the results are shown below. The test was carried out as follows. The compound was left on the hot-plate at 230 degrees Celsius for 5 minutes, and then the residual ratio was determined by HPLC.

| Compound | melting point Degrees Celsius | residual ratio % | Note |
| --- | --- | --- | --- |
| Compound (2) | >270 | >99 | invention |
| Compound (3) | >270 | >99 | invention |
| Compound (59) | >270 | >99 | invention |
| Compound (60) | >270 | >99 | invention |
| Comparative Compound | 214 | 83 | Comparative invention |

Comparative Compound

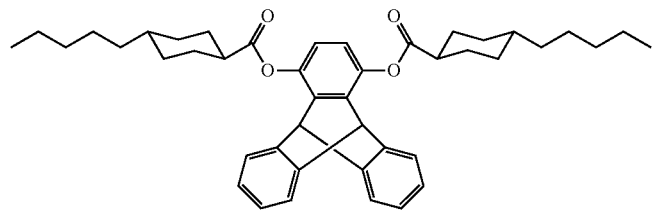 [SMILES: CCCCCC1CCC(C(=O)Oc2ccc(OC(=O)C3CCC(CCCCC)CC3)c3c2C2c4ccccc4C3c3ccccc32)CC1]

What is claimed is:

1. A compound having a triptycene moiety represented by formula (1):

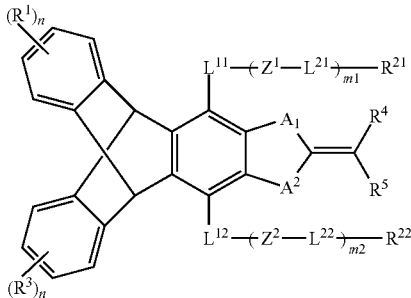

wherein $A^1$ and $A^2$ each respectively represents —S—, —O—, or —CO—;

$R^1$ and $R^3$ each respectively represents a substituent selected from the monovalent group consisting of a substituted or non-substituted $C_{1-15}$ linear aliphatic hydrocarbon group, substituted or non-substituted $C_{3-15}$ branched aliphatic hydrocarbon group, substituted or non-substituted $C_{3-15}$ cyclic aliphatic hydrocarbon group, substituted or non-substituted $C_{6-15}$ aryl group, amino group, or a substituent forming by bonding the substituent selected from the monovalent group and one selected from the divalent group consisting of a substituted or non-substituted alkylene group, substituted or non-substituted arylene group, substituted or non-substituted ester group, carbonate ester group, ether group and any combinations of two or more selected from them;

n is an integer from 0 to 2;

$R^4$ and $R^5$ each respectively represents an electron-withdrawing group having a Hammett's substituent constant $\sigma_p$ of equal to or more than 0, provided that $R^4$ and $R^5$ do not bond to each other to form a ring;

$L^{11}$, $L^{12}$, $L^{21}$ and $L^{22}$ each respectively represents a single bond or a divalent group selected from the group consisting of —O—, —S—, —S(=O)$_2$—, —CO—, —COO—, —COO—, —OCOO— and —NR$^A$— where $R^A$ represents a $C_{1-7}$ alkyl group or hydrogen atom, —CH$_2$— and any combinations thereof;

$Z^1$ and $Z^2$ each respectively represents a divalent 5- or 6-membered cyclic linking group;

$R^{21}$ and $R^{22}$ each respectively represents a hydrogen atom or substituted or non-substituted alkyl group; and m1 and m2 each respectively represents an integer of from 0 to 2.

2. The compound of claim 1, wherein, in formula (1), $Z^1$ and $Z^2$ each respectively represents 1,4-cyclohexylene or 1,4-phenylene.

3. The compound of claim 1, wherein, in formula (1), $A^1$ and $A^2$ are —S—.

4. The compound of claim 1, wherein, in formula (1), m1 and m2 each respectively represents 0 or 1.

5. The compound of claim 1, wherein, in formula (1), $L^{11}$ and $L^{12}$ each respectively represents —OC(=O)— or —C(=O)O—.

6. The compound of claim 1, wherein, in formula (1), $L^{21}$ and $L^{22}$ represent a single bond; and $R^{21}$ and $R^{22}$ each respectively represents a non-substituted alkyl group.

7. The compound of claim 1, wherein, in formula (1), $R^4$ and $R^5$ each respectively represents cyano or —C(=O)O—R' where R' represents a substituted or non-substituted $C_{1-15}$ alkyl group or substituted or non-substituted $C_{6-15}$ aryl group.

* * * * *